United States Patent
Zhang et al.

(10) Patent No.: US 9,533,283 B2
(45) Date of Patent: Jan. 3, 2017

(54) REGENERATION METHOD FOR CU-BTC MATERIAL

(71) Applicants: NANJING TECH UNIVERSITY (CN), Nanjing (CN); CHANGSHU YUTYRONE ADVANCED WEAR MATERIALS TECHNOLOGY CO., LTD. (CN), Changshu (CN)

(72) Inventors: Suoying Zhang, Nanjing (CN); Xiaohua Lu, Nanjing (CN); Wenjun Yao, Changshu (CN); Zhuhong Yang, Nanjing (CN); Changsong Wang, Nanjing (CN)

(73) Assignees: NANJING TECH UNIVERSITY, Nanjing (CN); CHANGSHU YUTYRONE ADVANCED WEAR MATERIALS TECHNOLOGY CO., LTD., Changshu (CN)

( * ) Notice: Subject to any disclaimer, the term of this patent is extended or adjusted under 35 U.S.C. 154(b) by 0 days.

(21) Appl. No.: 14/427,885

(22) PCT Filed: Oct. 10, 2012

(86) PCT No.: PCT/CN2012/082725
§ 371 (c)(1),
(2) Date: Mar. 12, 2015

(87) PCT Pub. No.: WO2014/056164
PCT Pub. Date: Apr. 17, 2014

(65) Prior Publication Data
US 2015/0246341 A1  Sep. 3, 2015

(51) Int. Cl.
*B01J 20/00* (2006.01)
*B01J 20/34* (2006.01)
(Continued)

(52) U.S. Cl.
CPC .......... *B01J 20/3475* (2013.01); *B01J 20/223* (2013.01); *B01J 20/226* (2013.01);
(Continued)

(58) Field of Classification Search
CPC . B01J 20/3475; B01J 20/28064; B01J 20/226; B01J 20/34; B01J 20/3458; B01J 20/223; B01J 20/3425; C07F 1/08; Y02C 10/08
See application file for complete search history.

(56) References Cited

U.S. PATENT DOCUMENTS

| | | | |
|---|---|---|---|
| 2012/0129684 A1* | 5/2012 | Vimont | B01D 53/8628 502/170 |
| 2012/0210872 A1* | 8/2012 | Duan | B01J 20/22 95/127 |

FOREIGN PATENT DOCUMENTS

| | | |
|---|---|---|
| CN | 103146183 | 1/2009 |
| CN | 1023896866 A | 3/2012 |

(Continued)

*Primary Examiner* — Jennifer A Smith
(74) *Attorney, Agent, or Firm* — Oliff PLC

(57) ABSTRACT

A method for regenerating a Cu-BTC material includes: impregnating a Cu-BTC adsorbed with guest molecules in an acidic proton solvent or in a steam environment thereof, and filtering the Cu-BTC material, to obtain a solid; impregnating the solid in a non-acidic organic solvent or a steam environment thereof, and finally filtering, washing and drying the solid, to complete the generation of the Cu-BTC material.

12 Claims, 2 Drawing Sheets

(51) Int. Cl.
  *B01J 20/22* (2006.01)
  *B01J 20/28* (2006.01)
  *C07F 1/08* (2006.01)

(52) U.S. Cl.
  CPC ... *B01J 20/28064* (2013.01); *B01J 20/28066* (2013.01); *B01J 20/28071* (2013.01); *B01J 20/3425* (2013.01); *B01J 20/3458* (2013.01); *C07F 1/08* (2013.01); *Y02C 10/08* (2013.01)

(56) References Cited

FOREIGN PATENT DOCUMENTS

| | | | | |
|---|---|---|---|---|
| JP | 2006-218348 | 8/2006 | | |
| JP | 2006-220173 | 8/2006 | | |
| KR | WO 2010136677 A1 * | 12/2010 | ......... | B01D 53/8628 |

\* cited by examiner

REGENERATION METHOD FOR CU-BTC MATERIAL

This application is the U.S. national phase of International Application No. PCT/CN2012/082725 filed on 10 Oct. 2012 which designated the U.S., the entire content of the International Application is hereby incorporated by reference.

TECHNICAL FIELD

The present invention belongs to the field of metal organic framework materials, particularly relates to a method for regenerating a Cu-BTC material.

RELATED ART

With the rapid development of global economy, the over-reliance of human beings on fossil fuels results in significant emissions of greenhouse gases such as $CO_2$, and causes a series of serious environmental problems, so $CO_2$ emission reduction becomes the urgent affair. However, with further researches, the energy costs behind $CO_2$ emission reduction cause widespread concern of the whole society. Taking the large contributor for $CO_2$ emission reduction, thermal power plant, as an example, by using the conventional organic amine adsorption method to capture 90% $CO_2$ in the flue gas, the energy consumption of the thermal power plant is increased by 25% to 40%, in which 80% energy is used for the regeneration of the adsorbing material. Therefore, the energy input for the regeneration of the adsorbing material directly determines the efficiency and effectiveness of the $CO_2$ capture system, and moreover, the porous material encounters the problem of difficult regeneration and regeneration cost when being used in wastewater treatment.

Metal organic frameworks (MOFs) are porous materials having a periodic network structure formed by metal ions or clusters and organic ligands through self-assembly, and have the advantages of large specific surface area, high porosity, and adjustable structure. Due the great advantages in gas adsorption and storage relative to commercial activated carbon and zeolite, MOFs are considered as the most promising gas adsorption and storage materials, and have attracted extensive attention in recent years. However, as for the adsorbing material, the stronger adsorption capacity always means higher energy costs for desorption, compared with molecular sieve and activated carbon, the processing capacity of the MOFs material on gases such as $CO_2$ and organic dyes is significantly improved, but the adsorbing material still needs to be regenerated through high-temperature, negative-pressure and ultrasound treatment, and the energy costs for regeneration are high. Furthermore, due to the existence of highly polar molecules such as $H_2O$ and $H_2S$, the adsorbing material is easily poisoned and deactivated during adsorption, thus further decreasing the regeneration efficiency of the adsorbing material.

As one of the most famous MOFs materials, Cu-BTC has been commercialized. Due to high stability and structural features such as unsaturated metal sites, Cu-BTC is widely considered as the most promising gas adsorption and capture material and wastewater treatment material. However, as described above, the existing regeneration techniques still adopt high temperature and negative-pressure activation, the energy consumption is high, and the problem of adsorbent deactivation cannot be solved.

SUMMARY

In view of the problems in the existing adsorption technique that the energy consumption for regeneration of the adsorbing material is high and the adsorbing material is easily poisoned, the present invention provides a method for rapidly regenerating a Cu-BTC material by switching a solvent or a steam environment at normal temperature and normal pressure. The method has the characteristics of moderate operating condition, complete desorption of guest molecules, and low energy costs.

The objective of the present invention can be achieved through the following measures:

A method for regenerating a Cu-BTC material is provided, including: impregnating Cu-BTC adsorbed with guest molecules in an acidic proton solvent or a steam environment thereof, and filtering the Cu-BTC material to obtain a solid; and impregnating the solid in a non-acidic organic solvent or a steam environment thereof, and finally filtering, washing and drying the solid, to complete the regeneration of the Cu-BTC material.

The guest molecules in the present invention refer to gas molecules and organic dye molecules, include various gas molecules and dye molecules that can be adsorbed by the Cu-BTC material, and specifically are one or more selected from $CO_2$, $CO$, $N_2$, $H_2$, $CH_4$, $C_2H_2$, $C_2H_4$, $NO$, $NO_2$, $SO_2$, $H_2S$, methyl orange, methyl blue, methylene blue, methyl red and Sudan red.

This method can be used to treat Cu-BTC materials with different adsorption capacities, and the adsorption capacity (that is, the mass fraction of the adsorbed molecules in the total amount of the material) is generally 0 to 100 wt %, and further the adsorption capacity is 0.1 wt % to 100 wt %, where the Cu-BTC material has different maximum adsorptions according to the saturated adsorption capacity of different molecules.

The Cu-BTC of the present invention is a porous high-specific surface area material having a specific surface area greater than 600 $m^2/g$. The regenerative Cu-BTC material before and after regeneration according to this method has a specific surface area greater than 600 $m^2/g$.

The acidic proton solvent in the present invention refers to a protic solvent having a pH value of less than 7, and is preferably at least one of acetic acid, formic acid, hydrochloric acid, sulfuric acid, nitric acid, carbonic acid, phosphoric acid, hydrofluoric acid, hydrogen bromide and hydrogen iodide. When the pH value of the acidic proton solvent of the present invention is 1 to 6, best regeneration effect can be achieved, and when the pH value is excessive low or high, the regeneration of Cu-BTC cannot be realized. When the concentration is excessively high, the structure of Cu-BTC may be decomposed, thus resulting in that Cu-BTC cannot be regenerated; when the concentration is excessively low, Cu-BTC cannot be desorbed and regenerated completely.

When Cu-BTC adsorbed with guest molecules is impregnated in an acidic proton solvent, the liquid volume is 20 folds mL/g of the solid mass; when the solid-liquid ratio is excessively low, Cu-BTC cannot be reacted and regenerated completely. Cu-BTC adsorbed with guest molecules is impregnated in an acidic proton solvent or a steam environment thereof for a duration of 1 min to 72 h, preferably, for a duration of 1 min to 10 h, and further preferably, for a duration of 1 min to 100 min.

When impregnating in a steam environment is adopted in the present invention, various steams can be prepared from different solvents by using existing methods and are used for impregnation, and preferably, saturated steams are used for impregnation.

The non-acidic organic solvent in the present invention refers to a non-acidic organic solvent having an pH value of greater than 7, and is preferably at least one of methanol, ethanol, N,N-dimethylformamide, dimethyl sulfoxide, acetonitrile, sulfolane, acetone, dimethylacetamide and hexamethylphosphoramide. The liquid volume of the non-acidic organic solvent is 10 folds mL/g and more of the solid mass. The solid is impregnated in the non-acidic organic solvent for a duration of 1 min to 72 h, preferably, for a duration of 1 min to 10 h, and further preferably, for a duration of 1 min to 100 min.

The present invention has the following beneficial effects:

1. The present invention has the advantage that the raw materials for regenerating the Cu-BTC material are commonly inexpensive industrial solvents, and the regeneration is carried out at normal temperature and normal pressure, so the reaction condition is more moderate and the energy costs are lower, compared with conventional high-temperature negative-pressure regeneration.

2. The present invention has the advantage that Cu-BTC is regenerated completely, and there is almost no difference in the adsorption capacity for guest molecules before and after regeneration.

The present invention has the advantages that the regeneration of Cu-BTC is rapid, and Cu-BTC can rapidly release the guest molecules by means of the action of the protic solvent.

BRIEF DESCRIPTION OF THE DRAWINGS

The disclosure will become more fully understood from the detailed description given herein below for illustration only, and thus are not limitative of the disclosure, and wherein.

DETAILED DESCRIPTION

Figure 1:
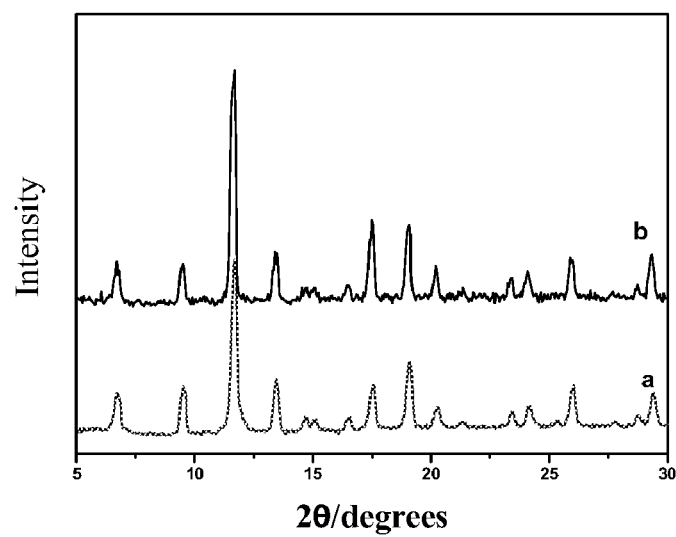
FIG. 1 is a comparison diagram of XRD patterns before and after regeneration of Cu-BTC in Embodiment 1, a) the structure of Cu-BTC before regeneration; b) the structure of Cu-BTC after regeneration.
Figure 2:
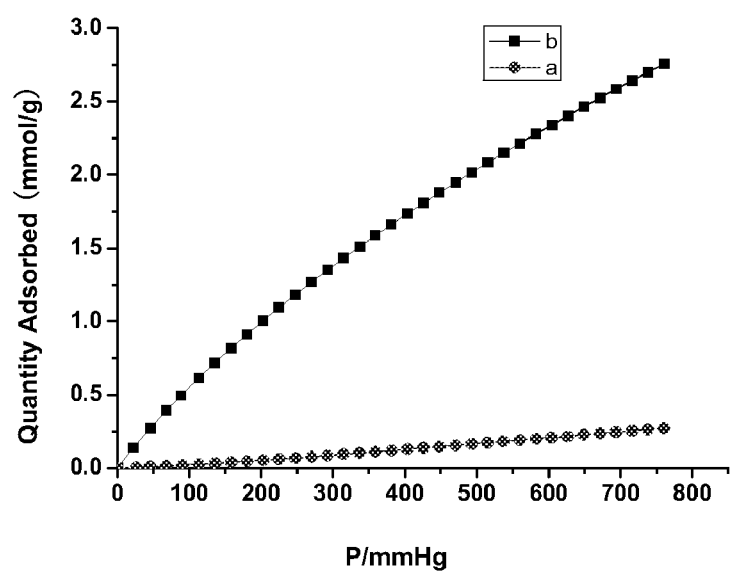
FIG. 2 shows $CO_2$ adsorption curves before and after regeneration of Cu-BTC in Embodiment 1, $CO_2$ adsorption curves a) before regeneration and b) after regeneration of Cu-BTC at normal temperature and normal pressure.

The present invention is further described below with reference to the following embodiments.

In the following implementation, the experimental methods are conventional methods unless otherwise stated; all reagents or raw materials are commercially available unless otherwise stated.

Embodiment 1

1 g $Cu_3 (C_9H_3O_6)_2 \cdot 3H_2O$ (Cu-BTC) adsorbed with saturated $CO_2$ having a specific surface area of 1123.6 $m^2/g$ and a pore volume of 0.46 $cm^3/g$ was impregnated in 50 ml hydrochloric acid solution at pH=1, reacted for 10 min with stirring and filtered to obtain a solid. The solid was impregnated in 50 ml N,N-dimethylformamide solution, reacted for 5 min with stirring, filtered out the solid and dried, to complete the regeneration of Cu-BTC. For the regenerated Cu-BTC, the specific surface area was 1052.7 $m^2/g$, and the pore volume was 0.46 $cm^3/g$.

Embodiments 2 to 10

Embodiments 2 to 10 were carried out according to the steps in Embodiment 1, and the raw materials and conditions for specific reactions were shown in Table 1. In Embodiment 9, the adsorbed guest molecules were organic dye molecules, and in Embodiment 10, a saturated steam was used for impregnation. The structure and the performance of the product were shown in Table 2.

TABLE 1

Raw materials and preparation conditions in Embodiments 2 to 10

| | | Control conditions | | | | | | |
|---|---|---|---|---|---|---|---|---|
| Other embodiments | Adsorbed guest molecules | Folds of liquid volume relative to the solid mass (mL/g) | Acid solution | pH of the solution | Duration min | Organic solvent | Folds of the organic solvent relative to the solid mass (mL/g) | Duration min |
| Embodiment 2 | $CO_2$ | 20 | nitric acid | 1 | 3 | dimethyl sulfoxide | 10 | 3 |
| Embodiment 3 | $N_2$ | 100 | acetic acid | 4 | 10 | methanol steam | 20 | 5 |
| Embodiment 4 | $C_2H_4$ | 30 | sulfuric acid | 2 | 5 | ethanol | 50 | 15 |
| Embodiment 5 | $H_2$ | 50 | nitric acid | 6 | 10 | sulfolane | 30 | 10 |
| Embodiment 6 | NO | 100 | phosphoric acid | 5 | 10 | acetonitrile | 40 | 10 |
| Embodiment 7 | $O_2$ | 50 | formic acid | 3 | 8 | dimethylacetamide | 30 | 10 |
| Embodiment 8 | $SO_2$ | 40 | sulfuric acid | 1.5 | 5 | hexamethylphosphoramide | 20 | 8 |
| Embodiment 9 | methyl orange | 50 | sulfuric acid | 1.5 | 5 | dimethylformamide | 30 | 8 |
| Embodiment 10 | $H_2S$ | / | hydrochloric acid steam | 3 | 60 | acetone steam | / | 30 |

TABLE 2

Structure and properties of the products of Embodiments 2 to 10

| | Structure and properties of the regenerated solid | | | |
|---|---|---|---|---|
| | Cu—BTC | | Cu—BTC (after regeneration) | |
| Other embodiments | specific surface area ($m^2/g$) | pore volume ($cm^3/g$) | specific surface area ($m^2/g$) | pore volume ($cm^3/g$) |
| Embodiment 2 | 1123.6 | 0.46 | 1105.3 | 0.46 |
| Embodiment 3 | 1123.6 | 0.46 | 1090.5 | 0.46 |

TABLE 2-continued

Structure and properties of the products of Embodiments 2 to 10

| | Cu—BTC | | Cu—BTC (after regeneration) | |
|---|---|---|---|---|
| Other embodiments | specific surface area ($m^2/g$) | pore volume ($cm^3/g$) | specific surface area ($m^2/g$) | pore volume ($cm^3/g$) |
| Embodiment 4 | 1123.6 | 0.46 | 1116.7 | 0.46 |
| Embodiment 5 | 1123.6 | 0.46 | 1108.4 | 0.46 |
| Embodiment 6 | 1123.6 | 0.46 | 1120.1 | 0.46 |
| Embodiment 7 | 1123.6 | 0.46 | 1078.6 | 0.46 |
| Embodiment 8 | 1123.6 | 0.46 | 1095.7 | 0.46 |
| Embodiment 9 | 1123.6 | 0.46 | 1054.3 | 0.46 |
| Embodiment 10 | 1123.6 | 0.46 | 1100.3 | 0.46 |

Comparative Example 1

1 g Cu-BTC adsorbed with saturated $CO_2$ having a specific surface area of 1123.6 $m^2/g$ and a pore volume of 0.46 $cm^3/g$ was impregnated in 50 ml hydrochloric acid solution at pH=6.5, reacted for 30 min with stirring and filtered to obtain a solid. The solid was impregnated in 20 ml N,N-dimethylformamide solution, reacted for 10 min with stirring, filtered out the solid and dried. The structure of the solid was changed, where the specific surface area was 320.76 $m^2/g$, and the pore volume was 0.25 $cm^3/g$.

Comparative Example 2

1 g Cu-BTC adsorbed with saturated $CO_2$ having a specific surface area of 1123.6 $m^2/g$ and a pore volume of 0.46 $cm^3/g$ was impregnated in 50 ml hydrochloric acid solution at pH=0.8, reacted for 5 min with stirring and filtered to obtain a solid. The solid was dried to obtain a white particle, and the solid was impregnated in 20 ml N,N-dimethylformamide solution, reacted for 10 min with stirring, filtered out the solid and dried. The structure of the solid was changed, where the specific surface area was 11.546 $m^2/g$, and the pore volume was 0.023 $cm^3/g$.

Comparative Examples 1 and 2 indicate that when the acid is excessively strong or weak, regeneration of Cu-BTC cannot be realized, and moreover, when the acid concentration is excessively low, the structure of the regenerated Cu-BTC is changed, Cu-BTC is directly decomposed and cannot be regenerated.

Comparative Example 3

1 g metal organic framework compound $Cu_3 (C_9H_3O_6)_2 \cdot 3H_2O$ (Cu-BTC) adsorbed with saturated $CO_2$ having a specific surface area of 1123.6 $m^2/g$ and a pore volume of 0.46 $cm^3/g$ was impregnated in 15 ml hydrochloric acid solution at pH=2, reacted for 10 min with stirring and filtered to obtain the reaction product. The reaction product was impregnated in 15 ml N,N-dimethylformamide solution, reacted for 5 min with stirring and filtered to obtain a solid. The solid was washed and dried, to obtain Cu-BTC, where the specific surface area was 810.25 $m^2/g$, and the pore volume was 0.36 $cm^3/g$.

Comparative Example 3 indicate that when the ratio of the liquid volume to the solid mass is too low, the guest molecules in Cu-BTC cannot be completely desorbed, and Cu-BTC cannot be completely regenerated.

What is claimed is:

1. A method for regenerating a Cu-BTC material, comprising:
    impregnating Cu-BTC adsorbed with guest molecules in an acidic proton solvent or a steam environment thereof, and filtering the Cu-BTC material to obtain a solid; and
    impregnating the solid in a non-acidic organic solvent or a steam environment thereof, and finally filtering, washing and drying the solid, to complete the regeneration of the Cu-BTC material; wherein the acidic proton solvent has a pH value of 1 to 6.

2. The method according to claim 1, wherein the guest molecules are gas molecules or organic dye molecules.

3. The method according to claim 1, wherein
    the specific surface area of the Cu-BTC adsorbed with guest molecules is greater than 600 $m^2/g$, and
    the specific surface area of the Cu-BTC material is greater than 600 $m^2/g$.

4. The method according to claim 1, wherein the acidic proton solvent is at least one member selected from the group consisting of acetic acid, formic acid, hydrochloric acid, sulfuric acid, nitric acid, carbonic acid, phosphoric acid, hydrofluoric acid, hydrogen bromide and hydrogen iodide.

5. The method according to claim 1 or 4, wherein
    when the Cu-BTC adsorbed with guest molecules is impregnated in the acidic proton solvent, a value of the liquid volume of the acidic proton solvent in milliliters is 20 folds or more than a value of the solid mass in grams; and
    the Cu-BTC adsorbed with guest molecules is impregnated in the acidic proton solvent or the steam environment thereof for a duration of 1 min to 72 h.

6. The method according to claim 1, wherein the non-acidic organic solvent is at least one member selected from the group consisting of methanol, ethanol, N,N-dimethylformamide, dimethyl sulfoxide, acetonitrile, sulfolane, acetone, dimethylacetamide and hexamethylphosphoramide.

7. The method according to claim 1, wherein a value of the liquid volume of the non-acidic organic solvent in milliliters is 10 folds or more than a value of the solid mass in grams.

8. The method according to claim 1, wherein the solid is impregnated in the non-acidic organic solvent for a duration of 1 min to 72 h.

9. The method according to claim 1, wherein the guest molecules are one or more members selected from the group consisting $CO_2$, $CO$, $N_2$, $H_2$, $CH_4$, $C_2H_2$, $C_2H_4$, $NO$, $NO_2$, $SO_2$, $H_2S$, methyl orange, methyl blue, methylene blue, methyl red and Sudan red.

10. The method according to claim 1, wherein the guest molecule adsorption in the Cu-BTC adsorbed with guest molecules is 0.1 wt % to 100 wt %.

11. The method according to claim 2, wherein the guest molecule adsorption in the Cu-BTC adsorbed with guest molecules is 0.1 wt % to 100 wt %.

12. A method for regenerating a Cu-BTC material, comprising:
    impregnating Cu-BTC adsorbed with guest molecules in an acidic proton solvent or a steam environment thereof, and filtering the Cu-BTC material to obtain a solid, wherein the solid is obtained without decomposing the structure of the Cu-BTC material; and
    impregnating the solid in a non-acidic organic solvent or a steam environment thereof, and finally filtering, washing and drying the solid, to complete the regeneration of the Cu-BTC material.

\* \* \* \* \*